| United States Patent [19] | [11] Patent Number: 4,595,788 |
| Yamamoto et al. | [45] Date of Patent: Jun. 17, 1986 |

[54] PROCESS FOR PRODUCING BUTADIENE

[75] Inventors: Haruhisa Yamamoto, Yokosuka; Kin-ichi Okumura, Takaoka, both of Japan

[73] Assignee: Nippon Zeon Co. Ltd., Tokyo, Japan

[21] Appl. No.: 674,786

[22] Filed: Nov. 26, 1984

[30] Foreign Application Priority Data

Nov. 25, 1983 [JP] Japan .................................. 58-221633
Dec. 14, 1983 [JP] Japan .................................. 58-234306

[51] Int. Cl.$^4$ .................................................. C07C 5/09
[52] U.S. Cl. .................................................. 585/621
[58] Field of Search .................................................. 585/621

[56] References Cited

U.S. PATENT DOCUMENTS 3,468,969  9/1969  Woerner .................................. 585/621

*Primary Examiner*—Curtis R. Davis
*Attorney, Agent, or Firm*—Sherman & Shalloway

[57] ABSTRACT

A process for producing butadiene which comprises (1) a reaction step of forming butadiene by gas-phase catalytic oxidative dehydrogenation of n-butene, (2) a cooling step of cooling the resulting gas discharged from the reaction step (1) to remove trace amounts of high boiling by-products contained in the resulting gas, (3) an aldehyde removal step of removing small amounts of aldehydes contained in the cooled gas discharged from the cooling step (2), (4) a compression step of compressing the gas discharged from the aldehyde removal step (3), and (5) a $C_4$ component recovery step of recovering a $C_4$ component containing butadiene and other $C_4$ hydrocarbons from the compressed gas discharged from the compression step (4).

9 Claims, 1 Drawing Figure

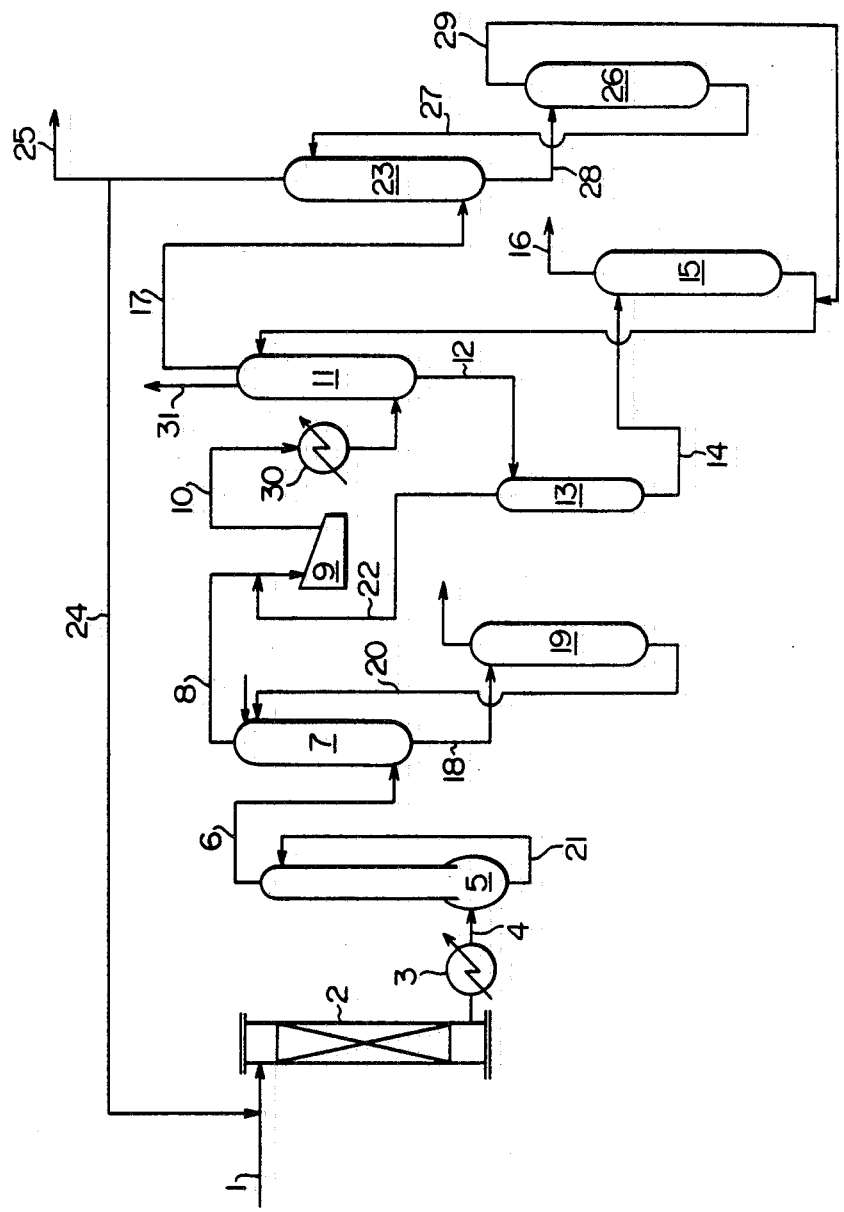

PROCESS FOR PRODUCING BUTADIENE

This invention relates to a process for producing butadiene. More specifically, this invention relates to a process for producing butadiene commercially advantageously by gas-phase catalytic oxidative dehydrogenation of n-butene.

Some methods of producing butadiene by subjecting n-butene to gas-phase catalytic oxidative dehydrogenation with molecular oxygen at high temperatures have been already commercially performed. However, these known methods generally use excess steam as a reaction diluent gas, and therefore suffer from defects that the steam cost is high, a large amount of a cooling water is needed at the point of cooling, and so forth (e.g. Hydrocarbon Processing, 1978, [11], 131; The Oil and Gas Journal, 1973, [3], 12). Moreover, in case the amount of oxygen fed to the reaction step for increasing a conversion of n-butene in these known methods, a concentration of oxygen present in the resulting gas after cooling increases, entailing a risk of explosion. It is therefore actually impossible to conduct a commercially profitable pressure absorption when recovering butadiene and other $C_4$ hydrocarbons from the formed gas.

The former defect can be eliminated by using as a diluent an off-gas (a waste gas obtained by removing from the reaction gas butadiene and other $C_4$ hydrocarbons, useful by-products such as furan, benzene, etc., high boiling substances and harmful by-products such as aldehydes, etc.) instead of the steam. The latter defect can be also remedied by relatively decreasing the oxygen concentration in the resulting gas with the use of the off-gas.

However, in case of increasing the conversion of n-butene by using the off-gas, when butadiene and other components are recovered from the resulting gas on pressure absorption, carbonaceous or high boiling tarry by-products are formed by pressurization and compression heat, and deposit on the inside of the compressor or the discharge portion, making the normal operation extremely difficult. This tendency is remarkable in particular when BBRR (the remaining $C_4$ fraction obtained by extracting butadiene and isobutene from the $C_4$ fraction) commercially available at low cost is employed as a starting material.

An object of this invention is to provide a process for producing butadiene commercially advantageously without involving the aforesaid defects.

The present inventors have made extensive studies to enable recovery of butadiene and other $C_4$ hydrocarbons from the resulting gas by pressure absorption even when the conversion of n-butene per passage through an oxidative dehydrogenation reaction zone is high or when BBRR containing trace amounts of isobutene, $C_5$ fractions, etc. is used as starting n-butene. As a result, they have discovered it is effective that aldehydes contained as by-products are removed before pressurizing the resulting gas.

This invention is to provide a process for producing butadiene which comprises (1) a reaction step of forming butadiene by gas-phase catalytic oxidative dehydrogenation of n-butene, (2) a cooling step of cooling the resulting gas discharged from the reaction step (1) to remove trace amounts of high boiling by-products contained in the resulting gas, (3) an aldehyde removal step of removing small amounts of aldehydes contained in the cooled gas discharged from the cooling step (2), (4) a compression step of compressing the gas discharged from the aldehyde removal step (3), and (5) a $C_4$ component recovery step of recovering a $C_4$ component containing butadiene and other $C_4$ hydrocarbons from the compressed gas discharged from the compression step (4).

Such a process of this invention will be concretely described by referring to an attached drawing which is a flow sheet illustrating a preferable embodiment of this invention.

From a line①n-butene, oxygen and a reaction diluent gas are introduced into the reaction step. Air is usually employed as an oxygen source. Steam, nitrogen or an off-gas (the remaining waste gas obtained by recovering a $C_4$ component and other useful components from the resulting gas) is properly used as a reaction diluent gas. Above all, the off-gas is preferably used from the aspects of economics and safety. It is appropriate that the off-gas content in the diluent gas is at least 30% by volume, preferably at least 50% by weight.

The reaction step is carried out in a reactor②held at high temperatures and packed with a catalyst where n-butene is oxidatively dehydrogenated to afford butadiene. The catalyst used can be properly chosen. Concrete examples thereof are catalysts developing beforehand by the present inventors (e.g. U.S. Pat. Nos. 4,423,281 and 4,336,409). A conversion of n-butene per passage through a catalyst layer is not limited in particular. Effectively, the conversion is at least 50%, especially at least 70%. The amount of oxygen fed into the reaction step is properly determined in consideration of an explosion limit in the compression step to be described later.

Where the conversion of n-butene is high, an amount of unreacted n-butene is small which eliminates the need of recycling. Therefore, BBRR containing a major proportion of butane showing little reactivity to the oxidative dehydrogenation reaction can be used as a starting material. In this case, it is profitable, for example, to employ BBRR composed of at most 85% of n-butene and in total at least 15% of n-butane and isobutane, said BBRR being commercially available at low cost.

In case of using BBRR as a starting material, said BBRR generally contains trace amounts of isobutene and $C_5$ fractions as impurities most of which are oxidized at the same time in the oxidative dehydrogenation reaction step to form aldehydes as by-products. The aldehydes are removed in the subsequent step. However, when excess aldehydes are secondarily formed, the load of the removal step increases. For this reason, it is suitable that the content of impurities (e.g. isobutene and $C_5$ fractions) that allow formation of aldehydes is set at not more than 7 mol%, preferably not more than 5 mol%.

The formed gas discharged from the reactor②is introduced into the heat removal step for properly lowering the temperature of the formed gas if necessary before introducing it into the cooling step. It is advisable to conduct said step commercially with a waste-heat boiler③On removing heat, the temperature of the formed gas is lowered to 220° to 150° C., preferably 200° to 170° C. The waste heat recovered is commonly converted to steam and reused. Where the heat is removed excessively from the formed gas in this step, trace amounts of high boiling by-products contained in the resulting gas deposit to clog the line. Care must be therefore taken in this step. In particular, when the conversion of butene increases or BBRR is employed as a starting material, the amounts of high boiling by-products greatly increase. Accordingly, the heat removal should be properly carried out.

The formed gas discharged from the heat removal step passes through a line ④ and is introduced into a cooling step of removing trace amounts of high boiling by-products contained in the formed gas and cooling the formed gas. Said step may be effected by dividing it into a step of removing the high boiling by-products and a step of cooling the formed gas. It is however advisable to perform both the steps at the same time. A quench column ⑤ is generally employed. Nevertheless, high boiling by-products deposit on a quench portion and such a trouble as clogging of the line or the column occurs frequently. A contrivance is thus required to prevent deposition of high boiling by-products.

In this step, a quenching method (e.g. Japanese Patent Pulication No. 6283/74) using oils such as paraffin oils, naphthene oils, etc. may be used, yet a quenching method using water is commercially advantageous. However, in case of the quenching method using water, high boiling by-products tend to deposit. To prevent the above deposition, it is effective that the formed gas passing through the line ④ is kept above 130° C., the inner wall surface of the column near the inlet through which to feed the formed gas into the quench column ⑤ is maintained above 120° C., and the formed gas and the spray water of 15° to 70° C. are thoroughly mixed and contacted with each other in the quench column.

Aldehydes contained in the formed gas are slightly removed in the quench column ⑤ but most of the aldehydes remain in the formed gas and are introduced into the aldehyde removal step via a line ⑥. Said step may be performed by any known devices if they are able to remove small amounts of the aldehydes contained in the formed gas. In general, said step is carried out by an aldehyde absorption column ⑦ and an aldehyde stripping column ⑲. In the aldehyde absorption column ⑦, aldehydes are separated by countercurrent contact with an aqueous solution of an organic acid until the content of aldehydes in the formed gas discharged from the aldehyde absorption column ⑦ reaches usually at most 0.4 mol%, preferably at most 0.2 mol%.

Aldehydes here separated are stripped in an aldehyde stripping column ⑲. The organic acid in the organic acid aqueous solution may be contained in a suitable concentration. Said organic acid may also be added from outside if required. Usually, organic acids secondarily formed together with butadiene in the reaction, such as acetic acid, acrylic acid, methacrylic acid, isobutyric acid, etc. are available. As for water, since part of the water content corresponding to the steam pressure in the formed gas passing through a line ⑥ is generally condensed in the column ⑦ this condensed water is circulated and used. When it is necessary to further add water, fresh water is separately introduced from top of the column ⑦. A packed column or a stage column is usually employed as the aldehyde absorption column ⑦ and the aldehyde stripping column ⑲. If required, a polymerization inhibitor is introduced to stop polymerization of aldehydes.

The formed gas discharged from the aldehyde absorption column ⑦ is subsequently introduced into a compression step of compressing the formed gas via a line ⑧. In this step, a compressor ⑨ is commonly used. The formed gas is usually compressed there to at least 2 atmospheres (gauge pressure), preferably at least 5 atmospheres (gauge pressure). Compression is conducted stepwise with a stage compressor. It is advisable to set a discharge temperature of each stage at 300° C. or below.

It is desirous that the concentration of oxygen in the formed gas introduced into the compressor ⑨ is not more than 6 mol%, preferably not more than 4 mol% to avoid a danger of explosion. It is desirable that the content of aldehydes in the formed gas is not more than 0.4 mol%, preferably not more than 0.2 mol%. Where excess aldehydes are present, carbonaceous or tarry substances are generated in the inside of the compressor and the discharge conduit by pressurization and compression heat, and deposit on the line, column, etc. Thus, troubles occur frequently. Occurrence of the carbonaceous or tarry substances poses no special problem in the short-term plant operation because of small amounts thereof. However, when the operation is run continuously for a long period of time of more than 10 days, said occurrence makes the operation extremely difficult. Any known compressors will do in this step.

The formed gas discharged from the compressor ⑨ is usually cooled with a direct cooling-type and/or indirect cooling-type heat exchanger ㉚ and then introduced into the $C_4$ component recovery step of recovering a $C_4$ component containing butadiene and other $C_4$ hydrocarbons from the formed gas. Said step is commonly effected by a $C_4$ component column ⑪ for separating the $C_4$ component contained in the formed gas with an absorption solvent by absorption, a stabilizer ⑬ for stripping small amounts of oxygen, nitrogen and carbon dioxide gas absorbed together with the $C_4$ component and a stripping column ⑮ for separating the $C_4$ component from the absorption solvent.

Examples of the absorption solvent are $C_5$–$C_{20}$ saturated hydrocarbons, $C_6$–$C_8$ aromatic hydrocarbons, butadiene dimer and other known substances. A packed column, a stage column and other usual columns are used as the $C_4$ component absorption column ⑪, the stabilizer ⑬ and the $C_4$ component stripping column ⑮.

The formed gas is, after separating the $C_4$ component in the absorption column ⑪ on absorption, discarded from a line ㉛ as an off-gas, or fed to an off-gas treatment step via a line ⑰.

Most of oxygen, nitrogen, carbon dioxide gas, etc. absorbed in the absorption solvent in small amounts and part of the $C_4$ component are stripped in the stabilizer ⑬. These gases are usually introduced just before the compression step via a line ㉒. The $C_4$ component is stripped in a $C_4$ stripping column ⑮ and fed to a butadiene purification step not shown through a line ⑯.

The off-gas discharged from the line ⑰ usually contains an absorption solvent (a $C_4$ component absorption solvent) of a $C_4$ component corresponding to a steam pressure. Where the off-gas is recycled to the reaction step (1), the $C_4$ component absorption solvent is oxidized in an oxidative dehydrogenation reaction zone to form substances unwanted in the process. Therefore, said solvent has to be removed in the off-gas treatment step. This step can be run in a known manner. Usually said step is effected through a $C_4$ component absorption solvent recovering column ㉓ and a separation column ㉖.

The off-gas discharged from the line ⑰ is treated in the $C_4$ component absorption solvent recovering column ㉓ such that the concentration of the $C_4$ component absorption solvent in the off-gas usually reaches at most 1 mol%. A treating method can be properly selected. A method wherein the off-gas is conacted countercurrently with a solvent composed of $C_8$–$C_{20}$ saturated hydrocarbons is commonly used.

The recovered solvent with the $C_4$ component absorption solvent absorbed is separated in a separation column (26). The $C_4$ component absorption solvent is recycled to the column (11) and the recovered solvent to the column (23) respectively.

Another method may be followed in place of the aforesaid method using the columns (23) and (26). For example, a method may be used wherein the off-gas discharged from the line (17) is passed through a catalyst zone for burning combustible substances contained in the off-gas either without, or after, passing through the column (23).

The thus treated off-gas is usable as a reaction diluent gas. In this instance, only a necessary amount of the off-gas is introduced into the reaction step and extra off-gas is discarded.

The composition, especially, the oxygen concentration of the off-gas used as the reaction diluent gas is measured. The proportions of the off-gas and air are determined such that the total concentration of oxygen in the off-gas and oxygen contained in air and fed to the reaction step is suited for the reaction conditions. Usually, the reaction conditions (oxygen concentration, n-butene concentration, etc.) can be freely determined by controlling the amount of air fed.

One example of the process in this invention has been thus far described according to the attached drawing. However, this invention is not limited to the process shown in the flow sheet of said drawing.

In accordance with this invention, irrespective of the conversion of n-butene, pressure absorption of the $C_4$ component can be conducted commercially safely and easily. Moreover even if the compressor is operated continuously for a long period of time, carbonaceous or tarry substances do not substantially occur, making it possible to prevent such a trouble as clogging of a line or a column. Accordingly, the process of this invention is especially effective when BBR containing a large amount of butane inert to the reaction, small amounts of isobutene liable to form aldehydes by oxidation and $C_5$ fractions is used as a starting material.

In the process of this invention, butadiene can be continuously produced industrially safely at low cost by using the off-gas as the reaction diluent gas. Particularly, the known method employing steam as a reaction diluent gas had a drawback that as the amount of the $C_4$ component in the formed gas and the concentration of unreacted oxygen greatly increase after removing the steam on condensation, explosive mixtures tend to occur during the operation. On the other hand, when the off-gas is used in the process of this invention, the formed gas is diluted with the reaction diluent gas in all steps except the step of stripping the $C_4$ component, so that even if a ratio of oxygen to starting n-butene is increased, no explosive mixtures result, and the conversion of n-butene per passage through the catalyst zone can be raised accordingly.

The following Examples illustrate this invention in more detail.

EXAMPLE 1

In accordance with this invention, butadiene was produced as follows.

(1) Reaction step:

An $Mo_{12}Bi_1Cr_3Ni_8K_{0.2}Pb_{0.5}$ catalyst (carrier silica) was prepared according to a method described in Example 1 of U.S. Pat. No. 4,423,281. This catalyst (600 ml) was packed in a stainless steel reaction line 1 inch in inner diameter and 2 m long, and heated to 365° C. on a metallic bath. A gas mixture composed of BBRR containing 26.6% of butane, 69.7% of n-butene and 3.7% of other $C_2$–$C_5$ hydrocarbons, air and nitrogen was passed through the catalyst layer.

In consequence, a conversion of n-butene per passage through the catalyst layer was 83.8 mol%, a yield of butadiene was 73.7 mol%, and a selectivity of butadiene was 87.9%. Small amounts of CO, $CO_2$, formaldehyde, acetaldehyde, furan, acetone, acrolein, methacrolein, benzene, methyl vinyl ketone, acetic acid, isobutyric acid, acrylic acid, methacrylic acid and maleic acid were formed as by-products. Trace amounts of high boiling by-products were also formed.

The thus obtained gas was composed mainly of 72.6 mol% of nitrogen, 2.1 mol% of oxygen, in total 2.4 mol% of argon, CO and $CO_2$, 9.6 mol% of water, 3.5 mol% of butane, 1.5 mol% of n-butene, 7.0 mol% of butadiene, 0.69 mol% of aldehydes and 0.05 mol% of an organic acid, and further contained trace amounts of furan, acetone, benzene, methyl vinyl ketone and high boiling by-products. The formed gas was produced at a rate of about 1.24 $m^2$ per hour (on NTP basis). The temperature of the formed gas at the outlet of the reactor was 365° C.

(2) Cooling step:

The thus formed gas was cooled to 180° C. and then introduced into a quench column via a line having an inner diameter of 12 mm and fully warmed. The temperature of the resulting gas just before the inlet of the quench column was 157° C.

The quench column was a spray column wherein an empty still 3 inches in inner diameter and 12 cm long was installed in a lower portion of an empty cylindrical line 1 inch in inner diameter and 1 m long. A formed gas introduction line was mounted in the empty still. The still was thoroughly warmed. The temperature of the inner wall surface of said still around which to introduce the formed gas was maintained at 152° C. by feeding the formed gas.

A spray nozzle was mounted on the upper portion of the column and water of 36° C. was circulated at a rate of 15 l per hour. Water was gradually increased by condensing part of the water content in the formed gas. The increased water content was therefore continuously drawn out.

The temperature of the formed gas discharged from top of the column was about 40° to 45° C. The composition of the formed gas was substantially the same as the formed gas introduced into the quench column except that aldehydes were 0.66 mol% and the organic acid was 0.02 mol%. Trace amounts of furan, acetone, benzene and methyl vinyl ketone in the formed gas were substantially the same as those in the formed gas introduced into the quench column. However, no high boiling by-products were observed at all because they were removed in the quench column.

(3) Aldehyde removal step:

The formed gas discharged from the cooling step was introduced into an aldehyde absorption column via a line 12 mm in inner diameter. The aldehyde absorption column was a packed column 3 inches in inner diameter and 3 m long, and the inside thereof was packed with a 5 mm$\phi \times$5 mm cylindrical Raschig ring. From top of the column, the organic acid aqueous solution after stripping aldehydes, which was cooled to 20° C., was fed at a rate of 15 l per hour. The organic acid contained in the organic acid aqueous solution was one obtained by dissolving the organic acid contained in the formed gas, and the organic acid might be contained in a suitable concentration. Water held at 20° C. was also supplied at a rate of 5 l per hour from top of the column. The formed gas introduced into the column was countercurrently contacted with this solution. Aldehydes contained in the formed gas were thereby absorbed and separated. The formed gas discharged from the aldehyde absorption column contained only 0.10 mol% of aldehydes. Organic acid, acetone and methyl vinyl ketone were little found in the formed gas. The composition of other components in said formed gas was substantially the same as that of other components in the formed gas introduced into the aldehyde absorption column. Part of the organic acid aqueous solution discharged from bottom of the aldehyde absorption column was subjected to waste water disposal, and the remainder was introduced into an aldehyde stripping column. Most of aldehydes, acetone and methyl vinyl ketone absorbed were stripped in said column and then recycled to the aldehyde absorption column.

(4) Compression step:

The formed gas discharged from the aldehyde removal step was introduced into a compressor via a line 12 mm in inner diameter. The compressor was of a diaphragm type, and the formed gas was compressed to 10 atmospheres (gauge pressure) by 2-stage compression. The discharged gas in each stage was cooled to 80° C.

The thus pressurized gas was further cooled to 35° C. by contacting it countercurrently with water.

(5) $C_5$ component recovery step:

The formed gas which had been compressed and cooled to 35° C. in the compression step was then introduced into a $C_4$ component absorption column to separate a $C_4$ component by absorption.

The $C_4$ component absorption column was a packed column 2 inches in inner diameter and 3 m long which was provided in the inside with a 5 mm$\phi \times$ 5 mm cylindrical Raschig ring. From top of the column, mixed xylene after stripping the $C_4$ component in the $C_4$ component stripping column, which was cooled to 8° C., was supplied at a rate of 4 l per hour. The formed gas introduced from bottom of the column was countercurrently contacted with the mixed xylene, and 99.4% of the $C_4$ component contained in the formed gas was absorbed.

The whole amount of the remaining aldehydes contained in the formed gas was absorbed in the xylene together with furan and benzene, stripped in the $C_4$ component stripping column along with the $C_4$ component and separated in the subsequent butadiene purification step. The gas free of the $C_4$ component, which was discharged from the $C_4$ component absorption column, was discarded as an off-gas after recovering xylene contained in the gas.

Xylene with the $C_4$ component absorbed was discharged from bottom of the $C_4$ component absorption column and entered into a stabilizer. Part of nitrogen, oxygen, $CO_2$ and the $C_4$ component dissolved in xylene were discharged in the stabilizer and then introduced into a $C_4$ component stripping column. The absorbed $C_4$ component, aldehydes, furan, benzene, etc. were stripped in the stripping column and recycled to the $C_4$ component absorption column.

(6) Results of operation:

The process comprising a series of the steps (1) to (5) was operated continuously for 62 days under substantially the same conditions. As a result, butadiene could be produced stably without observing a trouble caused by depositing carbonaceous or tarry substances during the operation.

EXAMPLE 2

In accordance with this invention, butadiene was produced as follows.

(1) Reaction step:

The same catalyst (600 ml) as used in Example 1 was packed in a stainless steel reactor 1 inch in inner diameter and 2 m long and heated to 365° C. on a niter bath. A gas mixture comprising air, BBRR and an off-gas discharged from the off-gas treatment step was passed therethrough. The gas mixture was composed mainly of, per unit hour, 867.5 l of nitrogen, 108.0 l of oxygen, 10.5 l of argon, 18.1 l of $CO_2$, 5.7 l of CO, 62.1 l of isobutane and n-butane, 122.4 l of n-butene and 7.3 l of other $C_2$–$C_5$ hydrocarbons (these components were all gaseous and the amounts were determined on NTP basis). Said gas mixture had further trace amounts of xylene, etc. contained in the off-gas.

As a result of the reaction, a conversion of n-butene per passage through the catalyst layer was 83.9 mol%, a yield of butadiene was 76.5 mol%, and a selectivity of butadiene was 91.2%. CO, $CO_2$, formaldehyde, acetaldehyde, furan, acetone, acrolein, methacrolein, benzene, methyl vinyl ketone, acetic acid, isobutyric acid, acrylic acid, methacrylic acid and maleic acid were formed in small amounts as by-products. Trace amounts of high boiling by-products were also formed.

The thus formed gas was composed mainly of 69.1 mol% of nitrogen, 2.3 mol% of oxygen, in total 3.7 mol% of argon, CO and $CO_2$, 10.2 mol% of water, 4.8 mol% of butane, 1.5 mol% of n-butene, 7.4 mol% of butadiene, 0.73 mol% of aldehydes and 0.05 mol% of organic acid, and contained trace amounts of furan, acetone, benzene, methyl vinyl ketone, and high boiling by-products. The resulting gas was produced at a rate of about 1.3 m$^3$ per hour (on NTP basis). The temperature of the resulting gas at the outlet of the reactor was 365° C.

(2) Cooling process:

The thus formed gas was cooled to 180° C. and subsequently introduced into a quench column via a line having an inner diameter of 12 mm and well warmed. The temperature of the formed gas just before the inlet of the quench column was 157° C.

The quench column was the same as used in Example 1, and the operating conditions thereof were the same as in Example 1.

The temperature of the formed gas discharged from top of the column was about 40° to 45° C. The composition of the formed gas was substantially the same as that of the formed gas introduced into the quench column except that aldehydes were 0.69 mol% and organic acid was 0.02 mol%. Trace amounts of furan, acetone, benzene and methyl vinyl ketone were substantially the same as those in the formed gas introduced into the quench column. No high boiling by-products were ascertained because said by-products were removed in the quench column.

(3) Aldehyde removal step:

The formed gas discharged from the cooling step was introduced into an aldehyde absorption column through a line 12 mm in inner diameter. The aldehyde absorption column was the same as used in Example 1, and the operating conditions thereof were the same as in Example 1.

The formed gas discharged from the aldehyde absorption column contained only 0.11 mol% of aldehydes. Organic acid, acetone and methyl vinyl ketone were scarcely ascertained in the formed gas. The composition of other components was substantially the same as that of other components in the formed gas introduced into the aldehyde absorption column. Part of the organic acid aqueous solution discharged from bottom of the aldehyde absorption column was subjected to waste water disposal and the reminder thereof was introduced into the aldehyde stripping column. Most of aldehydes, acetone and methyl vinyl ketone absorbed were stripped in the stripping column and then recycled to the aldehyde absorption column.

(4) Compression step:

The formed gas discharged from the aldehyde removal step was treated in the same way as in Example 1.

(5) $C_4$ component recovery step:

The formed gas which had been compressed and cooled to 35° C. in the compression step was introduced into a $C_4$ component absorption column to separate a $C_4$ component on absorption.

The $C_4$ component absorption column was the same as used in Example 1 and the operating conditions thereof were the same as in Example 1. Thus, 99.5% of the $C_4$ component contained in the formed gas was absorbed.

The whole amount of the remaining aldehydes contained in the formed gas was absorbed in xylene together with furan and benzene, stripped in the $C_4$ component stripping column together with the $C_4$ component, and separated in the subsequent butadiene purification step. The $C_4$ component-free off-gas leaving the $C_4$ component absorption column was then fed to an off-gas treatment step.

Xylene with the $C_4$ component absorbed was recycled to the $C_4$ component absorption column in the same manner as in Example 1.

(6) Off-gas treatment step:

The off-gas discharged from the $C_4$ component recovery step was introduced into a xylene recovery column through a line 12 mm in inner diameter. The xylene recovery column was a packed column 2 inches in inner diameter and 1 m long which was provided in the inside with a 5 mm$\phi \times$5 mm cylindrical Raschig ring. From top of the column, a light oil composed mainly of decanes after stripping xylene and cooled to 20° C. was fed at a rate of 1 l per hour. The off-gas introduced from bottom of the column was countercurrently contacted with the light oil to absorb substantially the whole amount of xylene contained in the off-gas. The light oil with xylene absorbed was stripped in a xylene stripping column and then recycled. The off-gas leaving the xylene recovery column contained xylene and decanes in negligible trace amounts.

The thus obtained off-gas contained 91.3 mol% of nitrogen, 3.5 mol% of oxygen, 1.1 mol% of argon, 3.1 mol% of $CO_2$, 0.9 mol% of CO and 0.1 mol% of the $C_4$ component. 609 l of the off-gas (gaseous, NTP base) was recycled to the reaction step as a reaction diluent gas and the remainder was discarded.

(7) Results of operation:

The process comprising a series of the steps (1) to (6) was operated continuously for 62 days under substantially the same conditions. As a result, butadiene could be produced stably without observing a trouble entailed in using the off-gas or a trouble caused by depositing carbonaceous or tarry substances during the operation.

What we claim is:

1. A process for producing butadiene which comprises (1) a reaction step of forming butadiene by gas-phase catalytic oxidative dehydrogenation of n-butene using as a reaction diluent gas a gas mixture which contains at least 30% by volume of an off-gas, (2) a cooling step of cooling the resulting gas discharged from the reaction step (1) to remove trace amounts of high boiling by-products contained in the resulting gas, (3) an aldehyde removal step of removing small amounts of aldehydes contained in the cooled gas discharged from the cooling step (2), (4) a compression step of compressing the gas discharged from the aldehyde removal step (3), and (5) a $C_4$ component recovery step of recovering a $C_4$ component containing butadiene and other $C_4$ hydrocarbons from the compressed gas discharged from the compression step (4).

2. The process of claim 2 wherein said BBRR is used as starting n-butene in the reaction step (1).

3. The process of claim 2 wherein said BBRR contains not more than 7 mol% of impurities that allow formation of aldehydes.

4. The process of claim 1 wherein prior to introducing the resulting gas discharged from the reaction step (1) into the cooling step (2), heat is removed to decrease the temperature to 220° to 150° C.

5. The process of claim 1 wherein the cooling step (2) consists of contacting the resulting gas with spray water in a quench column.

6. The process of claim 1 wherein the content of aldehydes in the formed gas discharged from the aldehyde removal step (3) is not more than 0.4 mol%.

7. The process of claim 1 wherein the concentration of oxygen in the formed gas introduced into the compression step (4) is not more than 6 mol%.

8. The process of claim 1 which further comprises an off-gas purification step (6) after the $C_4$ component recovery step (5) for removal of solvent used in the $C_4$ component recovery step (5).

9. The process of claim 8 wherein the purified off-gas discharged from the off-gas purification step (6) is recycled to the reaction step (1).

* * * * *

UNITED STATES PATENT AND TRADEMARK OFFICE
CERTIFICATE OF CORRECTION

PATENT NO. : 4,595,788
DATED : June 17, 1986
INVENTOR(S) : HARUHISA YAMAMOTO, ET AL.

It is certified that error appears in the above-identified patent and that said Letters Patent is hereby corrected as shown below:

```
Claim 2, line 1, (column 10, line 33),
        delete "claim 2", insert --claim 1--.
        delete "said".
```

Signed and Sealed this

Twenty-third Day of September 1986

[SEAL]

Attest:

DONALD J. QUIGG

Attesting Officer

Commissioner of Patents and Trademarks